(12) United States Patent
Marquez et al.

(10) Patent No.: US 8,062,359 B2
(45) Date of Patent: Nov. 22, 2011

(54) HIGHLY FLEXIBLE HEART VALVE CONNECTING BAND

(75) Inventors: Salvador Marquez, Foothill Ranch, CA (US); Derek Nguyen, San Clemente, CA (US); Diana Nguyen-Thien-Nhon, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 853 days.

(21) Appl. No.: 11/099,706

(22) Filed: Apr. 6, 2005

(65) Prior Publication Data

US 2006/0229719 A1    Oct. 12, 2006

(51) Int. Cl.
*A61F 2/24* (2006.01)
(52) U.S. Cl. ............ 623/2.41; 623/2.38
(58) Field of Classification Search .......... 623/2.1–2.41; A61F 2/06, 2/24
See application file for complete search history.

(56) References Cited

U.S. PATENT DOCUMENTS

| | | |
|---|---|---|
| 3,197,788 A | 8/1965 | Segger |
| 3,714,671 A | 2/1973 | Edwards et al. |
| 4,084,268 A | 4/1978 | Ionescu et al. |
| 4,259,753 A | 4/1981 | Liotta et al. |
| 4,291,420 A | 9/1981 | Reul |
| 4,297,749 A | 11/1981 | Davis et al. |
| 4,343,048 A | 8/1982 | Ross et al. |
| 4,388,735 A | 6/1983 | Ionescu et al. |
| 4,451,936 A | 6/1984 | Carpentier et al. |
| 4,470,157 A | 9/1984 | Love |
| 4,501,030 A | 2/1985 | Lane |
| 4,626,255 A | 12/1986 | Reichart et al. |
| 4,725,274 A | 2/1988 | Lane et al. |

(Continued)

FOREIGN PATENT DOCUMENTS

EP    0 084 395 B1    8/1986

(Continued)

OTHER PUBLICATIONS

Bernhard, et al., "A 'Semi-Supported' Porcine Xenograft—Description and First Clinical Use," Thorac, cardiovasc, Surgeon 37 (1989)/pp. 313-315.

(Continued)

*Primary Examiner* — Thomas J Sweet
*Assistant Examiner* — Jason-Dennis Stewart
(74) *Attorney, Agent, or Firm* — AnnMarie Kaiser; Guy L. Cumberbatch

(57) ABSTRACT

A connecting band for a highly flexible tissue-type heart valve having a stent with cusps and commissures that are permitted to move radially. The connecting band follows the cusps and commissures and extends outwardly. The valve is connected to the natural tissue along the undulating connecting band using conventional techniques, such as sutures. The connecting band may be a cloth-covered inner suture-permeable member and attaches to the underside of the valve at the cusps to provide support to the stent and to the outer side of the valve at the commissures. The connecting band includes commissure portions defining generally axial gaps that help permit flexing of the valve. The inner member may include one or more slits along the cusps to enhance flexibility. The inner member may further include a continuous outwardly projecting sewing ridge around its periphery which includes a series of ribs separated by grooves around the inflow edge of the cusps. The sewing ridge enables supra-annular implant of a valve constructed with the connecting band.

18 Claims, 12 Drawing Sheets

U.S. PATENT DOCUMENTS

| | | | |
|---|---|---|---|
| 4,778,461 A | 10/1988 | Pietsch et al. | |
| 4,851,000 A | 7/1989 | Gupta | |
| 5,071,431 A * | 12/1991 | Sauter et al. | 623/2.4 |
| 5,147,391 A | 9/1992 | Lane | |
| 5,163,953 A | 11/1992 | Vince | |
| 5,163,955 A | 11/1992 | Love et al. | |
| 5,258,023 A | 11/1993 | Reger | |
| 5,411,552 A | 5/1995 | Andersen et al. | |
| 5,449,384 A | 9/1995 | Johnson | |
| 5,489,297 A | 2/1996 | Duran | |
| 5,489,298 A | 2/1996 | Love et al. | |
| 5,500,016 A | 3/1996 | Fisher | |
| 5,549,665 A | 8/1996 | Vesely et al. | |
| 5,554,185 A | 9/1996 | Block et al. | |
| 5,697,382 A | 12/1997 | Love et al. | |
| 5,702,368 A | 12/1997 | Stevens et al. | |
| 5,716,417 A | 2/1998 | Girard et al. | |
| 5,728,152 A | 3/1998 | Mirsch, II et al. | |
| 5,800,527 A | 9/1998 | Jansen et al. | |
| 5,855,601 A | 1/1999 | Bessler et al. | |
| 5,861,028 A | 1/1999 | Angell | |
| 5,895,420 A | 4/1999 | Mirsch, II et al. | |
| 5,928,281 A | 7/1999 | Huynh et al. | |
| 5,935,163 A | 8/1999 | Gabbay | |
| 5,964,770 A | 10/1999 | Flomenblit et al. | |
| 6,074,419 A | 6/2000 | Healy et al. | |
| 6,102,845 A | 8/2000 | Woodard et al. | |
| 6,338,740 B1 | 1/2002 | Carpentier | |
| 6,558,418 B2 | 5/2003 | Carpentier et al. | |
| 6,736,845 B2 | 5/2004 | Marquez et al. | |
| 6,936,067 B2 * | 8/2005 | Buchanan | 623/2.28 |
| 2002/0173842 A1 | 11/2002 | Buchanan | |
| 2004/0059413 A1 | 3/2004 | Argento | |
| 2004/0148018 A1 | 7/2004 | Carpentier et al. | |
| 2006/0195184 A1 * | 8/2006 | Lane et al. | 623/2.38 |

FOREIGN PATENT DOCUMENTS

| | | |
|---|---|---|
| EP | 0 515 324 B1 | 12/1996 |
| GB | 2 279 134 A1 | 12/1994 |
| RU | 1806696 A1 | 4/1993 |
| WO | WO 90/11738 A1 | 10/1990 |
| WO | WO 92/12690 A1 | 8/1992 |
| WO | WO 93/18721 A1 | 9/1993 |
| WO | WO 95/28899 A1 | 11/1995 |
| WO | WO 97/46177 A1 | 12/1997 |
| WO | WO 98/43556 A1 | 10/1998 |
| WO | WO 00/00107 A1 | 1/2000 |
| WO | WO 00/64382 A2 | 11/2000 |
| WO | WO 00/67661 A2 | 11/2000 |

OTHER PUBLICATIONS

Jensen, et al., "New J-3 Flexible-Leaflet Polyurethane Heart Valve Prosthesis With Improved Hydrodynamic Performance," The International Journal of Artificial Organs/vol. 14/No. 10, 1991/pp. 655-660.

Krucinski, et al., "Numerical Simulation of Leaflet Flexure in Bioprosthetic Valves Mounted on Rigid and Expansile Stents," J. Biomechanics, vol. 26/No. 8, 1993/pp. 929-943.

* cited by examiner

LEAFLET ATTACHMENT LINE

LEAFLET ATTACHMENT LINE

HIGHLY FLEXIBLE HEART VALVE CONNECTING BAND

FIELD OF THE INVENTION

The present invention relates to prosthetic heart valves, and, more particularly, to a highly flexible prosthetic tissue valve and associated connecting band or sewing ring.

BACKGROUND OF THE INVENTION

Prosthetic heart valves are used to replace damaged or diseased heart valves. In vertebrate animals, the heart is a hollow muscular organ having four pumping chambers: the left and right atria and the left and right ventricles, each provided with its own one-way outflow valve. The natural heart valves are identified as the aortic, mitral (or bicuspid), tricuspid and pulmonary valves. The valves of the heart separate chambers therein, and are each mounted in an annulus therebetween. The annuluses comprise dense fibrous rings attached either directly or indirectly to the atrial and ventricular muscle fibers. Prosthetic heart valves can be used to replace any of these naturally occurring valves, although repair or replacement of the aortic or mitral valves are most common because they reside in the left side of the heart where pressures are the greatest. In a valve replacement operation, the damaged leaflets are excised and the annulus sculpted to receive a replacement valve.

The four valves separate each ventricle from its associated atrium, or from the ascending aorta (left ventricle) or pulmonary artery (right ventricle). After the valve excision, the annulus generally comprises a ledge extending into and defining the orifice between the respective chambers. Prosthetic valves may attach on the upstream or downstream sides of the annulus ledge, but outside of the ventricles to avoid interfering with the large contractions therein. Thus, for example, in the left ventricle a prosthetic valve is positioned on the inflow side of the mitral valve annulus (in the left atrium), or on the outflow side of the aortic valve annulus (in the ascending aorta).

Two primary types of heart valve replacements or prostheses are known. One is a mechanical-type heart valve that uses a ball and cage arrangement or a pivoting mechanical closure to provide unidirectional blood flow. The other is a tissue-type or "bioprosthetic" valve which is constructed with natural-tissue valve leaflets which function much like a natural human heart valve, imitating the natural action of the flexible heart valve leaflets which seal against each other to ensure the one-way blood flow.

Prosthetic tissue valves typically comprise a stent having a rigid, annular ring portion and a plurality of upstanding commissures to which an intact xenograft valve or separate leaflets of, for example, bovine pericardium are attached. Fabric covers a majority of the structure and a suture-permeable sewing ring is provided around the periphery for attaching to the natural annulus. Because of the rigidity of the material used in the stent and/or wireform, conventional valves have a diameter that is minimally affected by the natural motion of the heart orifice. In the aortic position, the prosthetic valve commissures extend axially in the downstream direction a spaced distance from the walls of the downstream aortic wall. Movement of the aortic wall or sinuses does not directly affect movement of the cantilevered commissures, though fluid flow and pressures generated by movement of the walls ultimately does cause the commissures to dynamically flex to some extent (i.e., they are cantilevered downstream in the aorta). Because of the inherent rigidity in conventional heart valves, the natural dilatation of the annulus is restricted, imposing an artificial narrowing of the orifice, and increasing the pressure drop therethrough.

One alternative to more rigid prosthetic aortic heart valves is seen in U.S. Pat. No. 6,558,418 to Carpentier, et al., and U.S. Pat. No. 6,736,845 to Marquez, et al., the disclosures of which are expressly incorporated by reference herein. Carpentier, et al. and Marquez, et al. disclose a flexible heart valve especially suitable for implant in the aortic position. A single or multi-element stent includes commissures constructed so that the cusps are pivotably or flexibly coupled together to permit relative movement therebetween. An undulating suture-permeable connecting band attached to the valve follows the cusps and commissures and extends outwardly such that the valve may be connected to the natural tissue using conventional techniques. The connecting band may be cloth-covered silicon and provides support to the stent and to the outer side of the valve at the commissures while still permitting the cusps to flex with respect to one another.

Despite serious attempts to create a flexible heart valve that responds to the natural motions of the annulus and downstream vessel walls, even more flexible valves are desirable.

SUMMARY OF THE INVENTION

The present invention provides a connecting band for a flexible heart valve that improves on earlier designs. In one embodiment, the connecting band features relief slits on the inner curvature of the cusps to facilitate flexing thereof. In another embodiment, the connecting band includes a more robust construction on the inflow side thereof that facilitates a supra-annular implant technique.

In accordance with a first aspect, the present invention provides a suture-permeable connecting band for securing a prosthetic heart valve to an anatomical cavity. The connecting band is flexible and has a continuous undulating shape generally defining a tube with alternating inflow cusps and outflow commissures, the cusps having large radii of curvatures relative to the commissures. An inflow edge of the connecting band substantially conforms to an outflow edge thereof and follows the undulating shape such that axial gaps are created between adjacent cusps at the commissures. The axial gaps having a height of at least about 50% of the overall axial height of the connecting band. Each cusp has a varying cross-section between adjacent commissures that includes at least one relief point at which the cross-section abruptly reduces such that bending of each connecting band cusp occurs first at the relief point. The connecting band may be molded of silicone rubber.

In one version, the relief point in each connecting band cusp comprises a generally radial slit. Desirably, there are a plurality of generally radial slits in each connecting band cusp, more preferably between about 5-7 slits. In an alternative version, the relief point in each connecting band cusp comprises a generally radial groove. Desirably, an inflow edge of each connecting band cusp comprises at least two generally radially-directed ribs separated by the generally radial groove. A plurality of generally radially-directed ribs and grooves may be provided that are angled toward the inflow direction, wherein the size of the ribs and grooves diminishes from a maximum at an apex of the cusps until they disappear prior to the commissures.

In accordance with another aspect of the invention, a suture-permeable connecting band for securing a prosthetic heart valve to an anatomical cavity, comprises a flexible, continuous connecting band having an inflow end and an outflow end. The connecting band exhibits an undulating shape generally circumscribing a tube with alternating inflow cusps and outflow commissures, the cusps having large radii of curvatures relative to the commissures. An inflow edge of the connecting band substantially conforms to an outflow edge thereof and follows the undulating shape such that axial gaps are created between adjacent cusps at the commissures, the gaps having a height of at least about 50% of the overall axial height of the connecting band. A continuous sewing ridge is provided around the periphery of the connecting band that is radially-outwardly directed at the commissures and larger and angled radially outward and toward the inflow end at the cusps. The sewing ridge facilitates supra-annular attachment of the prosthetic valve.

The connecting band may define a free margin comprising a relatively narrow flap that angles radially outward and toward the outflow end at the cusps, and is substantially axially-aligned at the commissures. Desirably, the free margin gradually diminishes in size from each commissure to an apex of each cusp. At the commissures, the free margin extends outward from the sewing ridge. Preferably, the sewing ridge at the cusps defines an inflow end of the connecting band and includes a plurality of alternating generally radial ribs and grooves. The size of the generally radial ribs varies and is greatest at an apex of each cusp, and a plurality of the alternating generally radial ribs and grooves may be provided, wherein the size of the ribs and grooves diminishes from a maximum at an apex of the cusps until they disappear prior to the commissures.

A method of supra-annular implantation of a flexible aortic prosthetic heart valve is also provided by the present invention. The method includes providing a flexible aortic prosthetic heart valve having a supporting structure to which prosthetic leaflets attach and project radially inward and to which a connecting band attaches and projects generally radially outward. The supporting structure and connecting band each generally circumscribe a tube and has an undulating shape with alternating inflow cusps and outflow commissures. The cusps have large radii of curvatures relative to the commissures. An inflow edge of the valve substantially conforms to an outflow edge thereof and follows the undulating shape such that axial gaps are created between adjacent cusps at the commissures. The gaps have a height of at least about 50% of the overall axial height of the supporting structure, and a continuous outwardly directed sewing ridge facilitates supra-annular attachment of the prosthetic valve. The method includes first removing the native leaflets at their line of attachment, then delivering the prosthetic heart valve to an aortic annulus, and finally implanting the prosthetic heart valve to the aortic annulus by securing the connecting band exclusively to fibrous tissue along the line of native leaflet attachment.

Each cusp of the connecting band may have a varying cross-section between adjacent commissures that includes at least one relief point at which the cross-section abruptly reduces such that bending of each connecting band cusp occurs first at the relief point. The relief point in each connecting band cusp may comprise a generally radial slit. Alternatively, the relief point in each connecting band cusp comprises a generally radial groove, and wherein an inflow edge of each connecting band cusp comprises at least two generally radially-directed ribs separated by the generally radial groove. In any event, the method includes securing the commissures of the prosthetic valve to the fibrous native leaflet commissures such that the valve cusps are subjected to bending forces in use and the radial slit or radial groove enhances flexibility of the cusps.

DESCRIPTION OF THE PREFERRED EMBODIMENTS

The present invention provides a sewing ring or connecting band for a highly flexible aortic heart valve that is attached generally along a scalloped or undulating perimeter downstream from where the natural leaflets were originally attached. The natural leaflets include arcuate cusp portions separated by common commissure portions. If the natural valve has three leaflets, and has a vertically oriented flow axis, the leaflets are evenly distributed circumferentially 120° apart with lower (upstream) cusp portions and upper (downstream) generally axially aligned commissure portions. The annular root of the native aortic valve is composed of fibrous tissue and generally conforms to the undulating perimeter of the valve to support the leaflets. In this respect, implanting a prosthetic aortic heart valve of the present invention involves typically excising the natural leaflets and then attaching the prosthetic heart valve proximate the fibrous annulus. Certain embodiments may be attached a short distance up the aortic wall, although attachment entirely to the fibrous annulus may be preferred. Various attachment means may be used, including sutures, staples, adhesives, or other similar expedients.

Figure 1:
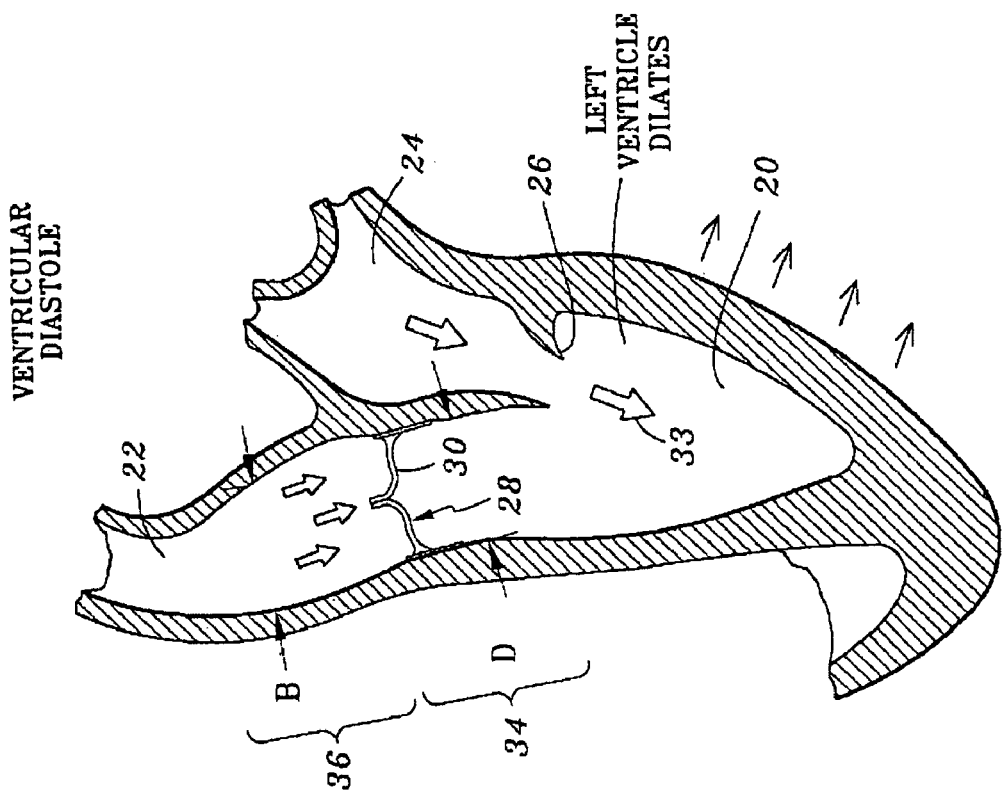
FIG. 1 is a sectional view through the left half of a human heart showing a systolic phase of left ventricular contraction.
Figure 2:
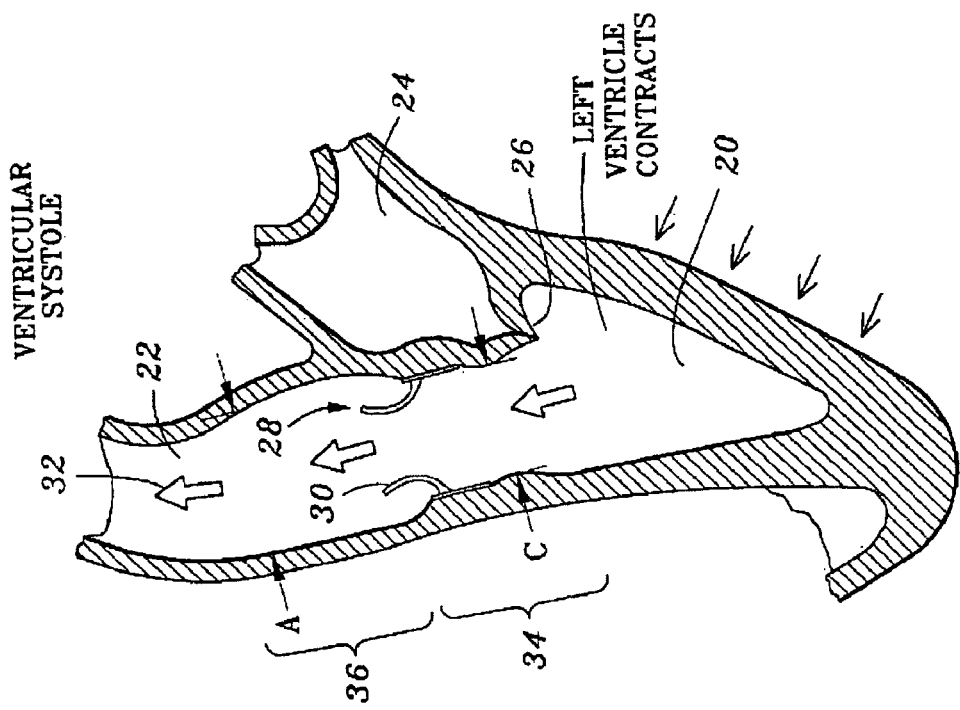
FIG. 2 is a sectional view through the left half of a human heart showing a diastolic phase of left ventricular expansion.

To better illustrate the advantages of a flexible heart valve constructed with a connecting band of the present invention, an understanding of the relative movement of the annulus and aorta is helpful. In this regard, FIGS. 1 and 2 illustrate the two phases of left ventricular function, systole and diastole. Systole refers to the contraction or pumping phase of the left ventricle when the aortic valve opens, while diastole refers to the expansion or filling phase during which the aortic valve is closed. FIGS. 1 and 2 illustrate in cross section the left chamber of the heart with the left ventricle 20 at the bottom, and the ascending aorta 22 and left atrium 24 diverging upward from the ventricle to the left and right, respectively.

FIG. 1 illustrates systole with the left ventricle 20 contracting, while FIG. 2 illustrates diastole with the left ventricle dilating. The aortic valve 28 is schematically illustrated here as having leaflets 30. As mentioned, the native aortic valve has a tri-leaflet structure. Contraction of the ventricle 20 causes the mitral valve 26 to close and the aortic valve 28 to open, and ejects blood through the ascending aorta 22 to the body's circulatory system, as indicated in FIG. 1 by the arrows 32. Dilation of the ventricle 20 causes the aortic valve 28 to close and mitral valve 26 to open, and draws blood into the ventricle from the left atrium 24, as indicated in FIG. 2 by the arrows 33.

The walls of the left chamber of the heart around the aortic valve can be generally termed the annulus region 34 and the sinus region 36. The annulus region 34 defines an orifice that is the narrowest portion between the ventricle 20 and ascending aorta 22, which as noted above is composed of fibrous tissue. The sinus region 36 is that area just downstream (up in the drawing) from the annulus region 34 and includes somewhat more elastic, less fibrous tissue. Specifically, the sinus region 36 typically includes three identifiable, generally concave sinuses (formally known as Sinuses of Valsalva) in the aortic wall intermediate the upstanding commissures of the valve 28. The placement of the sinuses corresponds to the location around the annulus periphery of the three leaflets. The sinuses are relatively elastic and are constrained by the intermediate, more fibrous commissures of the aortic annulus. That is, the annulus region 34 and sinus region 36 are not discretely separated into either fibrous or elastic tissue, as the fibrous annulus extends a short distance axially into the sinus region 36 at the three commissures.

The sinuses tend to move in and out to facilitate fluid dynamics of the blood in conjunction with systole and diastole. During systole, as seen in FIG. 1, the sinus region 36 expands somewhat to a diameter A. This facilitates blood flow through the ascending aorta 22 to the rest of the body. In contrast, during the diastolic phase as seen in FIG. 2, the sinus region 36 contracts somewhat to a smaller diameter B and help close the three leaflets. The diameters A and B are intended to be a measurement of the radial movement of the commissure regions of the valve 28. In this regard it will be understood that the cross-sections shown are not taken in a single plane, but instead are taken along two planes angled apart 120° with respect one another and meeting at the midpoint of the aorta 22. The sinus region 36 has a neutral, or relaxed diameter (not shown) somewhere in between diameters A and B.

The annular region 34 also moves in and out during the systolic and diastolic phases. As seen in FIG. 1, the annular region 34 contracts somewhat to a diameter C during systole. In contrast, during the diastolic phase as seen in FIG. 2, the annular region 34 expands somewhat to a larger diameter D. Much like the sinus region 36, the annular region 34 has a neutral, or relaxed diameter (not shown) somewhere in between diameters C and D.

As will be explained more fully below, a highly flexible prosthetic valve of the present invention accommodates the in-and-out movements of both the annular region 34 and the sinus region 36. That is, alternating peripheral portions of the prosthetic valve are attached to the annular region 34 and the sinus region 36, or adjacent thereto, and move accordingly. It is important to point out that the preceding discussion of dynamic movement of the annulus and sinus regions is based on preliminary understanding of such movement. That is, direct measurements of these movements are problematic, and thus certain assumptions and predictions must be made. The actual dynamic movement in any particular human heart may be different, but the principles of the present invention would still apply. Certainly, relative movement in the annulus and sinus regions during systole and diastole does exist, and the highly flexible prosthetic heart valve of the present invention accommodates such movement.

Figure 3:
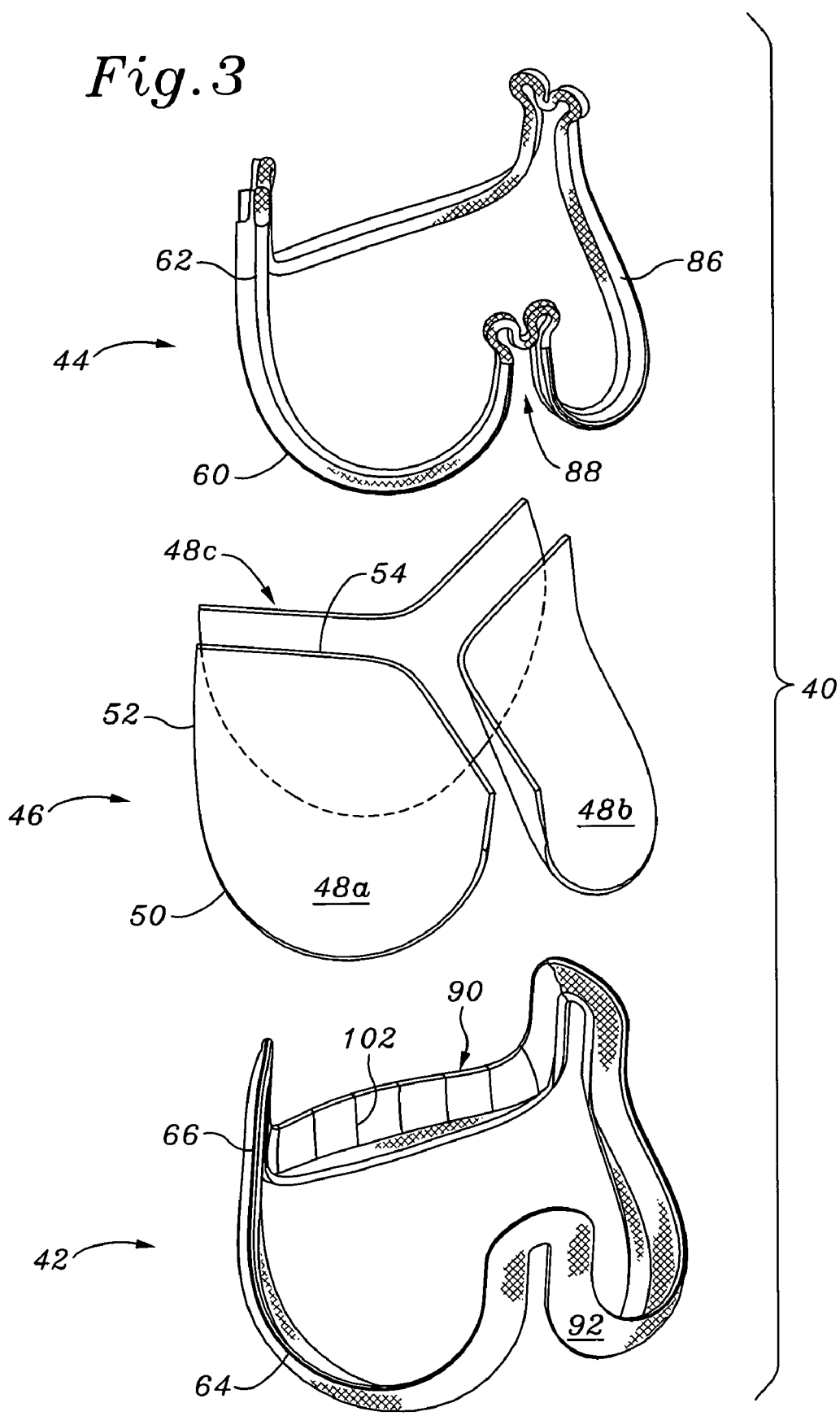
FIG. 3 is an exploded perspective view illustrating subassemblies of a prosthetic heart valve having an exemplary connecting band of the present invention.
Figure 7:
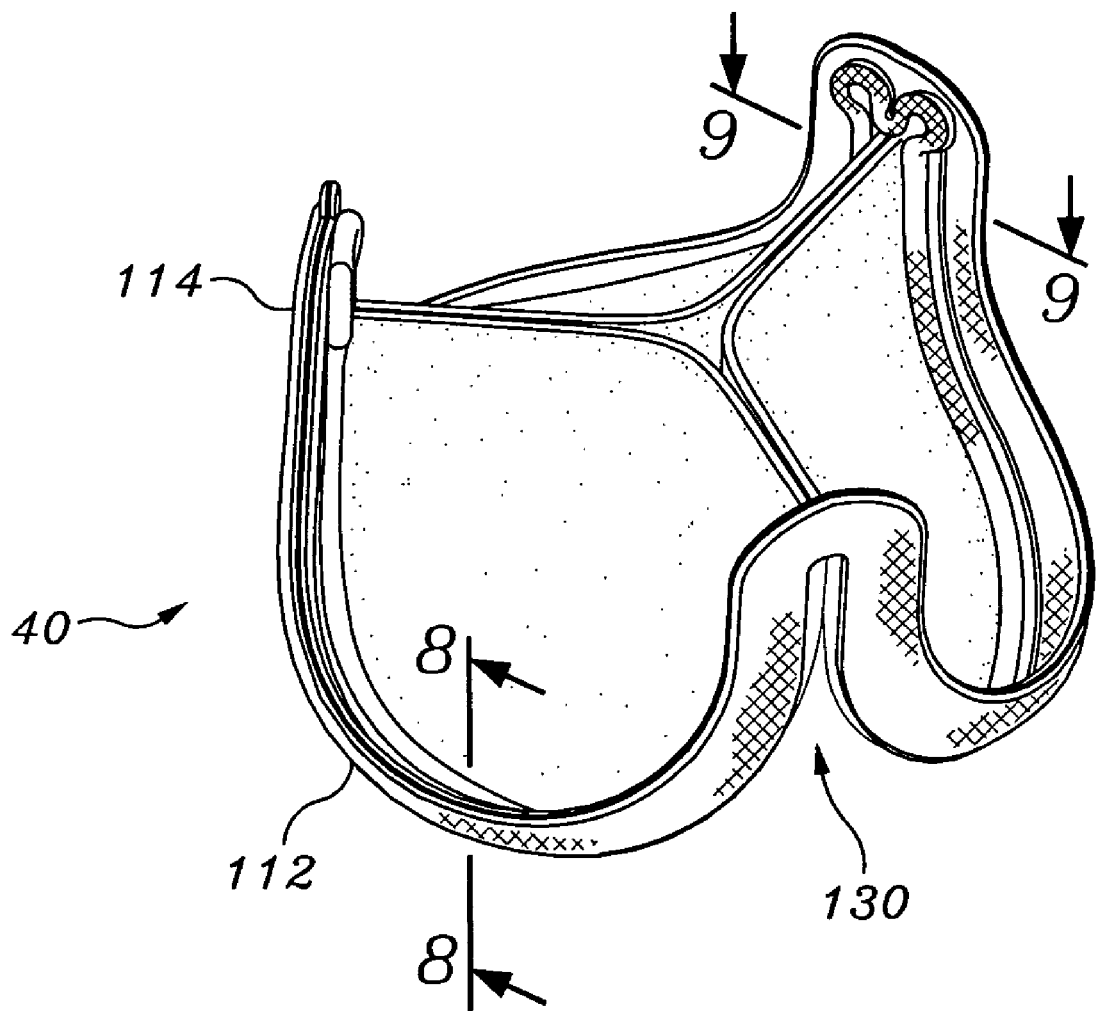
FIG. 7 is a perspective view of an assembled prosthetic heart valve of the present invention.

With reference now to FIG. 3, the primary sub-assemblies of a preferred embodiment of a flexible prosthetic heart valve 40 having a connecting band 42 of the present invention are shown in exploded view. For purposes of discussion, the directions up and down, upper and lower, or top and bottom, are used with reference to FIG. 3, but of course the valve can be oriented in any direction both prior to and after implantation. From top to bottom, the heart valve 40 comprises a stent assembly 44, a group 46 of three leaflets 48a, 48b, 48c, and the connecting band 42. Each of the sub-assemblies seen in FIG. 3 is procured and assembled separately (except for the group of leaflets, as explained in U.S. Pat. No. 6,558,418), and then joined with the other sub-assemblies to form the fully assembled valve 40 as seen in FIG. 7.

The prosthetic valve 40 is a trifoliate valve with three leaflets 48a, 48b, 48c. Although three leaflets are preferred, and mimic the natural aortic valve, the principles of the present invention can be applied to the construction of a prosthetic valve with two or more leaflets, depending on the need.

Each of the sub-assemblies seen in FIG. 3 includes three cusps separated by three commissures. The leaflets 48 each include an arcuate lower cusp edge 50 terminating in upstanding commissure edges 52. Each leaflet 48 includes a coapting or free edge 54 opposite the cusp edge 50. In the assembled valve 40, the cusp edges 50 and commissure edges 52 are secured around the periphery of the valve, with the free edges 54 permitted to meet or "coapt" in the middle. The stent assembly 44 also includes three cusps 60 separated by three upstanding commissures 62. In like manner, the connecting band 42 includes three cusp portions 64 separated by three upstanding commissure portions 66.

Figure 4:
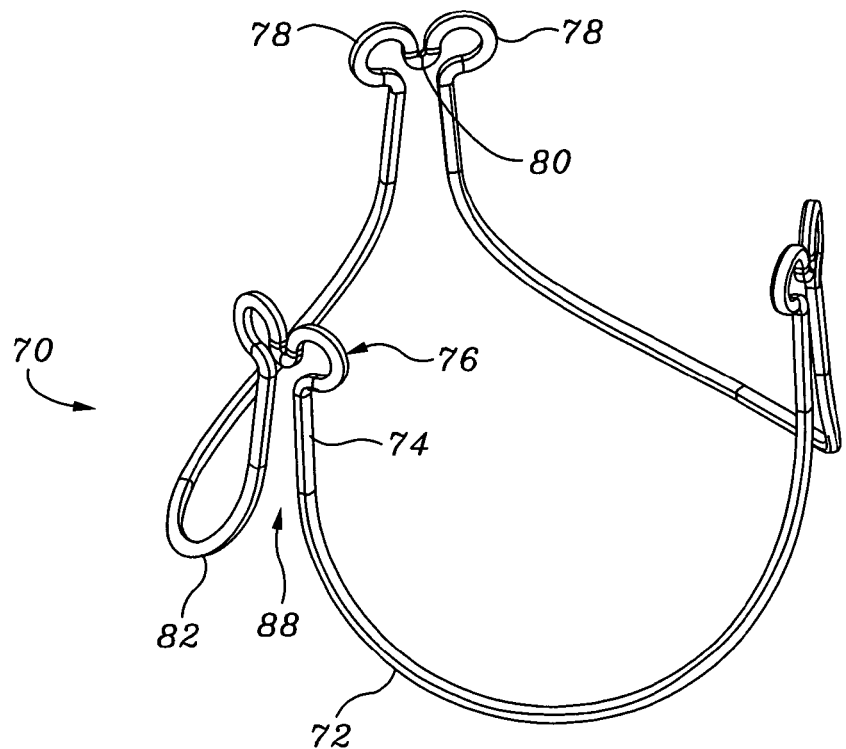
FIG. 4 is an elevational view of an internal stent of the heart valve FIG. 3.

An inner stent 70 of a preferred stent assembly 44 is seen in FIG. 4. The stent assembly 44 also comprises an outer cloth cover as shown in FIG. 3. As was described in U.S. Pat. No. 6,558,418, the inner stent 70 may comprise three identical and separate stent members, each of which has a separate cloth covering. However, as shown in FIG. 4, the inner stent 70 desirably comprises a single element generally circumscribing a tube with an undulating shape defined by alternating inflow cusp regions 72 and outflow commissure regions 74. The arcuate cusp regions 72 have large radii of curvatures relative to the upstanding commissure regions 74, each of which terminate at a tip 76. The inner stent 70 preferably comprises an elongated rod- or wire-like member made out of an elastic biocompatible metal and/or plastic alloy, such as Elgiloy®, Nitinol, polypropylene, etc. The stent 70 may be bent into the illustrated shape, using conventional wire-forming techniques. The material selected for the inner stent 70 should be elastic to permit flexing along their lengths, but should possess a minimum of stiffness to avoid asymmetric deformation of the constructed valve 40. The stent 70 supplies an inner frame for the valve 40 that is relatively more rigid than the other components. Therefore, the stent 70 acts to limit total flexibility of the valve 40.

In one particular construction, the stent 70 comprises a single element of Nitinol that is originally severed in a predetermined pattern from a flat sheet and then be formed into the three-dimensional shape shown. The formation method may include heat setting, one example of which is provided in U.S. Patent Application Document No. 2004/0078950, the disclosure of which is expressly incorporated by reference herein. The resulting structure has a rectilinear cross-section, which is desirably electropolished to remove sharp edges.

As seen at the top in FIG. 4, each commissure tip 76 includes a pair of nearly circular outer flexure portions 78 connected by an oppositely-curved inner bridge portion 80. The flexure portions 78 project in the outflow direction, while the bridge portion 80 projects in the inflow direction. The resulting shape resembles mouse ears. The flexure portions 78 each possess a relatively large radius of curvature relative to the spacing and nearly 360° change of direction between adjacent commissure regions 74. The flexure portions 70 enhance the ability of the cusp regions 72 of the stent 70 to move with respect to one another. That is, the larger bend radius thus provided at the commissure tips 76 relative to a simple inverted U-shape, as in conventional heart valves, provides a longer moment arm between the points where adjacent commissure regions 74 end. Furthermore, the cross sectional shape and size of the flexure portions 78 may be designed to further enhance the flexibility of the stent 70.

In a still further alternative, a portion of the tips 76, such as the bridge portions 80, may be designed to break after certain number of movement cycles of the stent 70, so that the structural support within the valve 40 separates into individual cusps. Such a design is seen in U.S. patent application Ser. No. [Insert ECV-5783 serial number], the disclosure of which is hereby expressly incorporated by reference.

Alternatively, the material for the stent 70 may be highly flexible so as to add relatively little reinforcement to the valve 40. For example, the inner stent 70 may be formed of a length of medical grade silicone that provides some physical structure that helps in stitching fabric around the valve, and also helps provide some bulk for grasping and sewing the valve in place, but otherwise does not reduce the flexibility of the other components. In this case, the commissures 76 are inherently flexible, enabling the cusp regions 72 to flex or pivot with respect to one another. This very high flexibility of the valve 40 minimizes any unwanted impediment to the natural annulus and aortic wall movement, and desirably maximizes the flow orifice formed though the valve, thus reducing any pressure loss therethrough. The highly flexible stent material may be provided in one or multiple filaments, with or without a surrounding enclosing sleeve, and may be silicone as mentioned, polypropylene, Delrin, polyurethane, polytetrafluoroethylene (PTFE), or the like. An exemplary thickness of the highly flexible stent material is about 0.011-0.013 inches for a monofilament version, or up to 0.025 inches with multiple filaments.

Each of the commissure tips 76 is positioned slightly radially inward with respect to the arcuate cusp regions 72. A gradual radially outward bend 82 is provided in the stent 70 at a transition between each of the commissure regions 74 and the intermediate cusp region 72. This bend 82 permits the inner stent 70 to remain in a tubular configuration. That is, if the cusp regions 72 extended in a plane between each of the commissure regions 74, the plan view would be somewhat polygonal. Instead, each of the cusp regions 72 includes a lower apex, and the apices of all of the cusps define a circle concentric with and having the same diameter as a circle defined by all of the tips 76. The stent 70 thus defines a substantially cylindrical volume therewithin. Of course, other volumes may be defined by the stent 70 wherein the tips 76 define a circle that is smaller or larger than a circle defined by the apices. For example, the apices may be provided outward from the tips 76 so the stent 70 defines a frusto-conical volume therewithin.

As seen in FIG. 3, the inner stent 70 is preferably covered with a generally tubular cloth. The cloth cover is a biocompatible fabric, such as polyethylene terephthalate, and includes a tubular portion closely conforming around the inner stent 70 and a flap 86 extending radially outward therefrom. The cloth cover is formed by wrapping an elongated sheet of fabric around the inner stent 70 and joining the free edges with sutures to form the flaps 86. As can be seen in the valve cross-sections of FIGS. 8 and 9, the flap 86 extends from the stent 70 in a direction that is generally outward with respect to the cusp region 72, and continues in the same general orientation up the commissure regions 74 to the tips 76.

The stent assembly 44 provides an inner support frame that is generally rigid along the cusp regions 72 of the inner stent 70, but which permits the cusp regions to move with respect to one another. In this context, "generally rigid" refers to the structural strength of the inner stent 70 that is sufficient to maintain the general shape, especially during delivery and implant, but that permits some flexing at the commissure regions 74. More particularly, the inner stent 70 provides nodes or pivot points of the valve 40 at the commissures 62 of the stent assembly 44. Because of these nodes, the cusp regions 72 are permitted to move radially inward and outward with the motion of the surrounding anatomy. Inward pivoting is permitted by spaces 88, seen in FIG. 4, defined between adjacent commissure regions 74 of the inner stent 70. These regions 88 are generally triangular and gradually increase in size from the attached commissure tips 76 to the diverging cusp regions 72.

Figure 5:
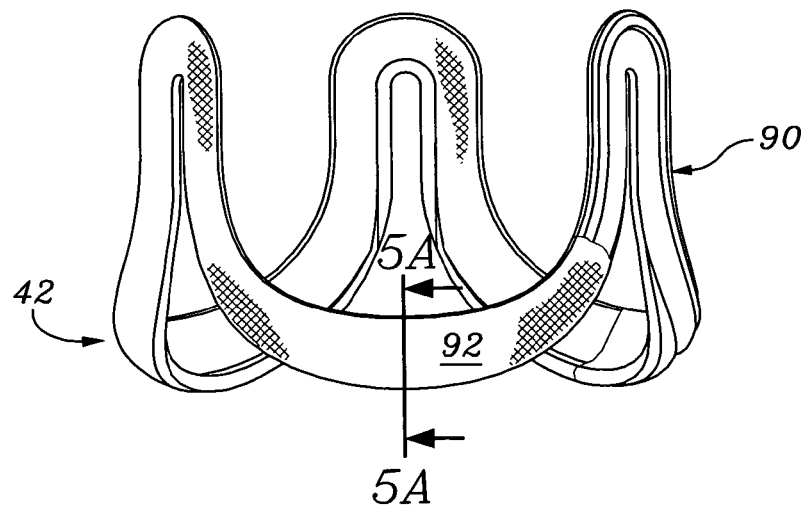
FIG. 5 is a partially cut-away elevational view of a fabric-covered connecting band of the prosthetic heart valve of the present invention.
Figure 6:
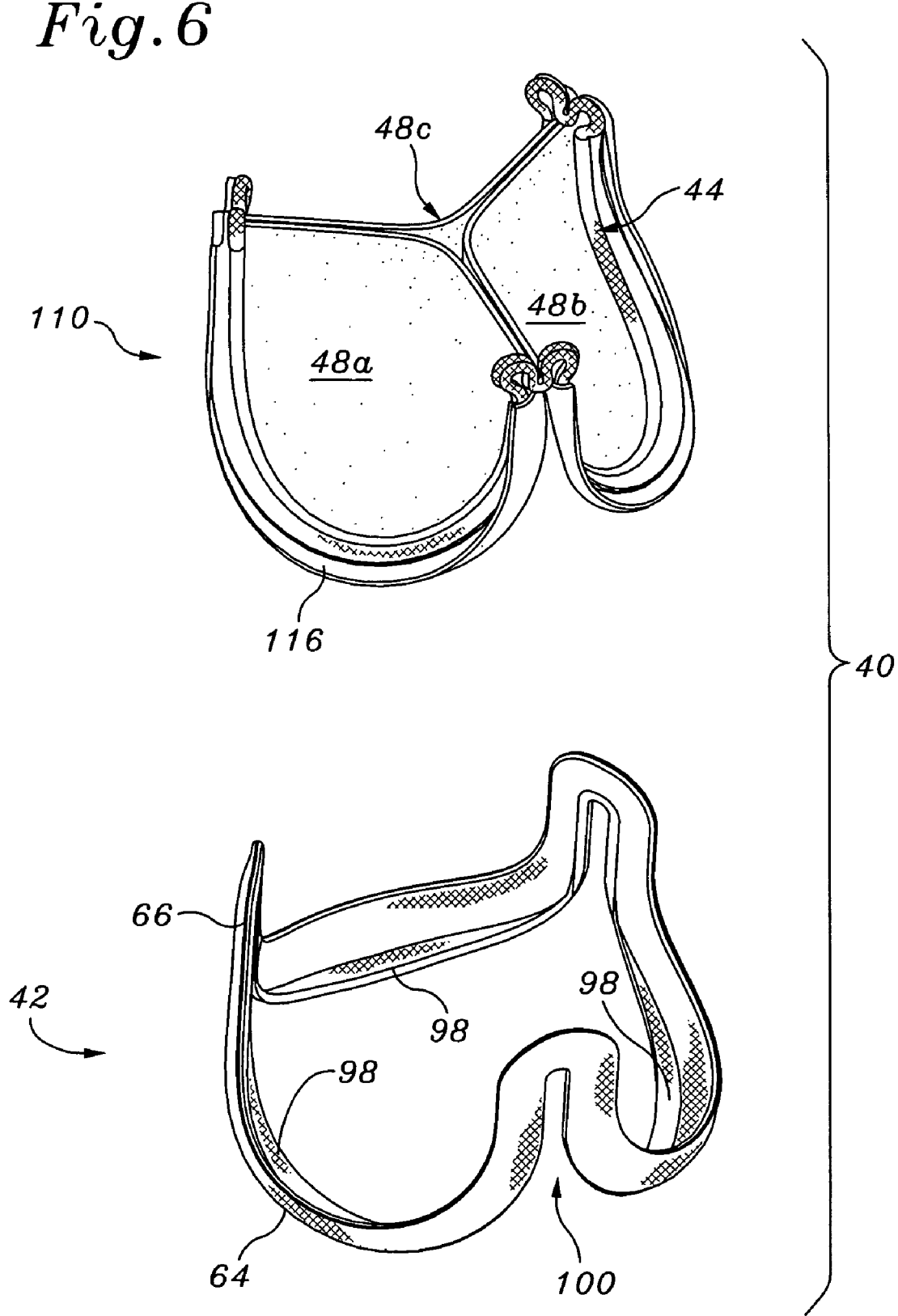
FIG. 6 is an exploded perspective view of the heart valve of FIG. 3 partially assembled.

FIGS. 3, 5 and 6 illustrate in more detail the connecting band 42 that comprises an inner member 90 surrounded by a cloth cover 92 (shown partially cutaway in the figures). As mentioned previously with respect to FIG. 3, the connecting band 42 includes cusp portions 64 alternating with commissure portions 66. The continuous undulating connecting band 42 mirrors the shape of the stent assembly 44, generally circumscribing a tube and having an undulating shape with three cusp portions 64 alternating with three commissure portions 66, the cusps having large radii of curvatures relative to the commissures. This shape is provided by the inner member 90, with the cloth cover 92 closely wrapped therearound and sewn closed. In a preferred embodiment, the inner member 90 is a suture-permeable material such as molded silicone rubber, and the cloth cover 92 is polyethylene terephthalate. While the stent assembly 44 provides structural support for the leaflets 48, the connecting band 42 supplies an interface between the prosthetic valve 40 and the surrounding anatomy such that sutures or staples may be used for implantation. In this context, the term "suture-permeable" refers to materials that may be punctured not just with sutures but also with staples and the like.

Figure 5A:
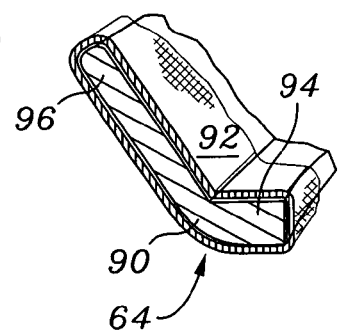
FIG. 5A is a sectional view of a fabric-covered connecting band of the prosthetic heart valve of the present invention.

The inner member 90 has a varying cross sectional shape from cusp portion to commissure portion. FIG. 5A is cross-section through one of the cusp portions 64 of the connecting band 42, and shows a region of the inner member 90 having an inner ledge 94 and upwardly angled outer flap or free margin 96. The cloth-covered ledges 94 extend generally radially inward and define three stent supports 98 of the connecting band 42, as seen in FIG. 6. The ledge 94 has its greatest radial dimension at the midpoint or apex of each of the cusp portions 64 and gradually tapers down in size toward the commissure portions 66.

Figure 9:
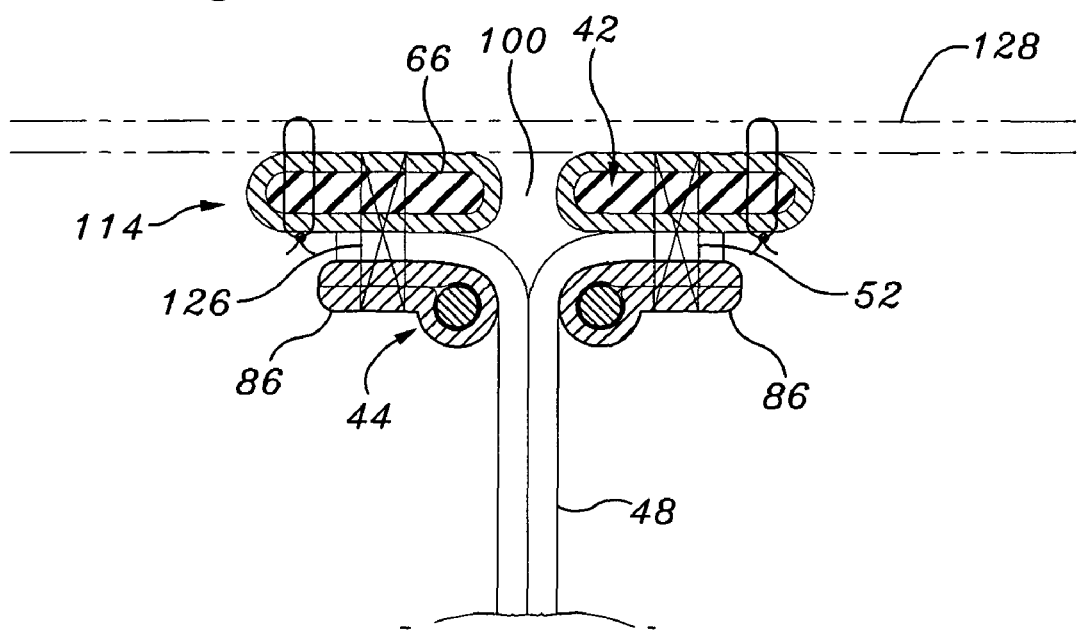
FIG. 9 is a cross-sectional view through a commissure of the prosthetic heart valve of the present invention, taken along line 9-9 of FIG. 7, and showing a portion of the host aortic wall in phantom.

As seen in the cross-section of the FIG. 5A, the free margins 96 form their greatest outward angle with respect to a central axis of the connecting band 42 at each cusp portion 64, and gradually re-align to be parallel to the central axis in the commissure portions 66. The cross-section of the inner member 90 at the commissure portions 66 is seen in FIG. 9. With reference to FIG. 6, the commissure portions 66 of the connecting band 42 define generally axial gaps 100 that help permit flexing of the valve 40. It should be noted that the connecting band 42 may be discontinuous at the commissure portions 66 if the valve has bioresorbable commissures and is designed to separate into individual "leaflets."

The connecting band 42 provides enhanced flexibility with respect to earlier connecting bands for flexible valves. FIG. 3 illustrates an exemplary arrangement of generally radial gapless cuts or slits 102 formed in the free margins 96 of each of the cusps of the inner member 90. The slits 102 extend from the outflow edge of the free margin 96 to a maximum length terminating at a corner between the free margin 96 and the radial ledge 94 (see FIG. 5A). There is preferably at least one slit 102 in each cusp of the inner member 90 that extends between two commissures. Ideally, there are at least two slits 102, and more preferably between five to seven. Because the slits 102 open to the inside radius of the curvature of each cusp region 64, they provide the relief points within the material of the inner member 90 along that edge and facilitate spreading apart of the commissure regions 66 of the connecting band 42 during flexing of the prosthetic valve 40. In addition to the slits 102, the weave or construction of the cloth covering 92 on the connecting band may have greater elasticity in the circumferential direction than in the radial direction around the cusp regions 64.

Figure 8:
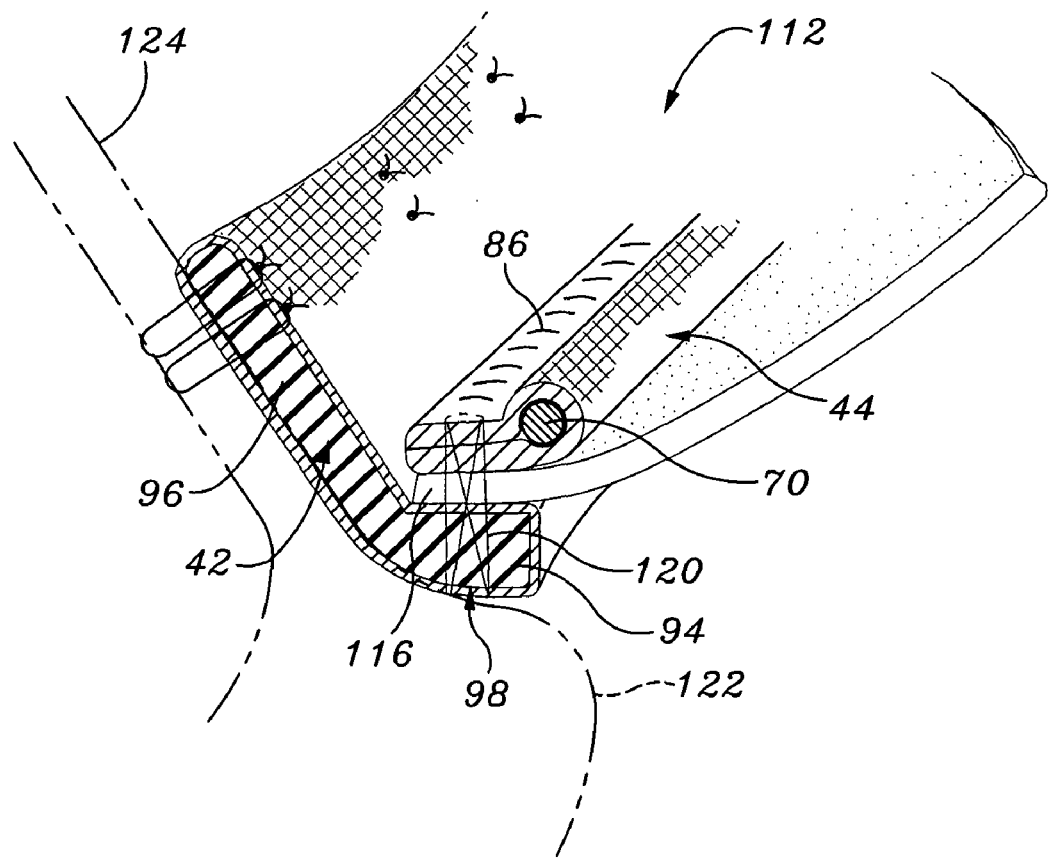
FIG. 8 is a cross-sectional view through a cusp of the prosthetic heart valve of the present invention, taken along line 8-8 of FIG. 7, and showing a portion of the host annulus in phantom.

FIG. 6 also illustrates a sub-assembly 110 in which the leaflets 48 are secured to the stent assembly 44, while FIG. 7 illustrates the assembled valve 40 in perspective, and FIGS. 8 and 9 show cross-sections through a valve cusp 112 and valve commissure 114, respectively. The peripheral shape of the valve 40, defined by the combined stent assembly 44 and connecting band 42, generally circumscribes a tube and has an undulating shape with alternating inflow cusps 112 and outflow commissures 114, and the leaflets extend inward therefrom to provide flexible flow occluding surfaces.

Preferably, the leaflets 48 are pre-attached to align the free edges 54 (FIG. 3). The free edges 54 of each two adjacent leaflets 48 extend outward in juxtaposition and are received within the triangular space 88 (FIG. 3) defined between the commissure regions 74 of the stent assembly 44. The group of assembled leaflets 46 is thus "inserted" underneath the stent assembly 44 until the juxtaposed free edges 54 of the leaflets 48 are in close proximity below the cloth-covered tips 76 of the stent. An outer margin 116 of each leaflet 48 is folded underneath the corresponding cusp 60 of the stent assembly 44. At this point, sutures or other such means attach the margins 116 to the flap 86 of the stent assembly 44, as seen in the cross-section section of FIG. 8. A more complete description of an assembly procedure for the leaflets 48 and stent assembly 44 is provided in U.S. Pat. No. 6,558,418 to Carpentier, et al.

With reference to the cross-section of FIG. 8, the sandwiched configuration of the stent assembly 44, leaflet 48, and connecting band 42 can be seen. The connecting band 42 is sewn or otherwise attached to the exterior of the stent/leaflet subassembly 110 (FIG. 6). Actually, the connecting band 42 is attached underneath the stent/leaflet subassembly 110 at the cusps, but the free margins 96 of the connecting band are positioned to the outside of the subassembly. More specifically, the cloth flap 86 of the stent assembly 44 aligns with the leaflet margins 116, which in turn rest on the stent supports 98. A series of suture stitches 120 are used to secure these elements together. Preferably, the flap 86 terminates at the same location as the margin 116 of each leaflet 48, and at the corner defined in the connecting band 42 between each ledge 94 and free margin 96. The radially innermost wall of the ledge 94 is preferably inward from or at least axially below the stent 70. This supporting construction helps prevent the stent 70 from migrating downward with respect to the connecting band 42. The host annulus 122 is seen in phantom with the aortic wall 124 continuing upward therefrom. It can be readily seen that the angled shape of the cusp portions 64 of the connecting band 42 conform nicely to the host annulus and adjacent sinular region.

Now with reference to FIG. 9, the assembly of the valve components in the commissure region is seen. The commissure edges 52 of each of the leaflets 48 are sandwiched in between the stent assembly 44 and connecting band 42. More particularly, the commissure edges 52 are sandwiched between the flaps 86 and the generally planar commissure portions 66 of the connecting band 42 (FIG. 6). Sutures 126 are provided to join these elements together. The commissure edges 52 preferably terminate at the same location as the flaps 86. FIG. 9 shows in phantom a portion of the aortic wall 128 to which the commissures 114 of the valve 40 are attached. Again, the particular attachment means is not shown, but the connecting band 42 is traditionally sutured to the wall 128.

FIG. 9 also illustrates the gap 100 provided in the commissure regions of the connecting band 42, and the lack of structural connection between the two sides of each valve commissure 114. With reference to FIG. 7, the prosthetic valve 40 exhibits three gaps 130 at the commissures 114 that provide the desired flexibility. The gaps 130 are created by the gaps 88 in the stent assembly 44 and the gaps 100 in the connecting band 42. The gaps 130 preferably extend a majority of the height of the valve from an inflow and at the lowest apex of the cusps 112 into close proximity with the commissure tips. In a preferred embodiment, the gaps 130 extend at least about 50% of the entire 10 height of the valve to enable the cusps 112 to move with respect to one another, preferably between about 55-75%, and more preferably about 65%.

Figure 18:
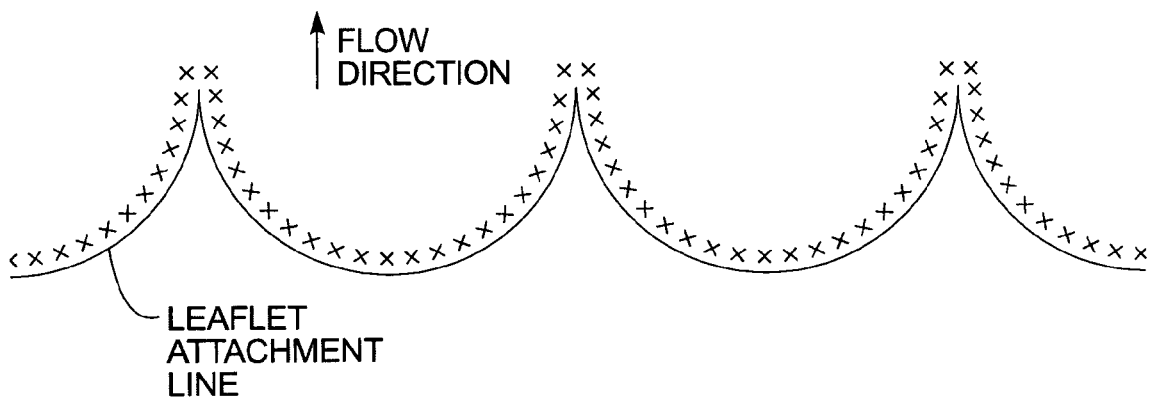
FIG. 18 schematically illustrates an intra-sinular suture placement relative to a solid leaflet attachment line.

The prosthetic heart valve 40 of FIGS. 3-9 is particularly suitable for intra-sinular placement in the aortic position. That is, the cusps 112 are typically positioned just to the outflow side of the aortic annulus, while the commissures 114 extend up above the native commissures to the aortic wall, in the region of the sinuses. FIG. 18 is a schematic illustration of this implant scheme, with the solid line depicting a flattened undulating native leaflet attachment line, and the row of Xs indicating the intra-sinular placement of sutures or staples to attach a prosthetic valve. In particular, the suture line is positioned slightly to the outflow side of the annulus, potentially within the weaker tissue of the wall of the ascending aorta. Some surgeons express concern about possible aortic damage from attaching the connecting band 42 of the valve 40 of FIGS. 3-9 to the aortic wall, as opposed to the fibrous annular tissue. Furthermore, if a surgeon ignores the prescribed intra-sinular placement of sutures, and instead uses a standard interrupted annular suture technique, the valve 40 would end up in an intra-annular position because of the enlarged free margin 96 of the connecting band 42. The term "intra-annular position" refers to the location within the inwardly projecting annulus. This position has been the conventional implant location for more rigid heart valves, which, as mentioned above, tends to reduce the orifice size and thus the blood flow therethrough. Although opinions vary, there is a need for a highly flexible prosthetic heart valve that can be attached entirely to the annulus in a "supra-annular" position. The term "supra-annular position" refers to a location just downstream from the inwardly projecting annulus, along the line that the native leaflets attach.

Figure 10:
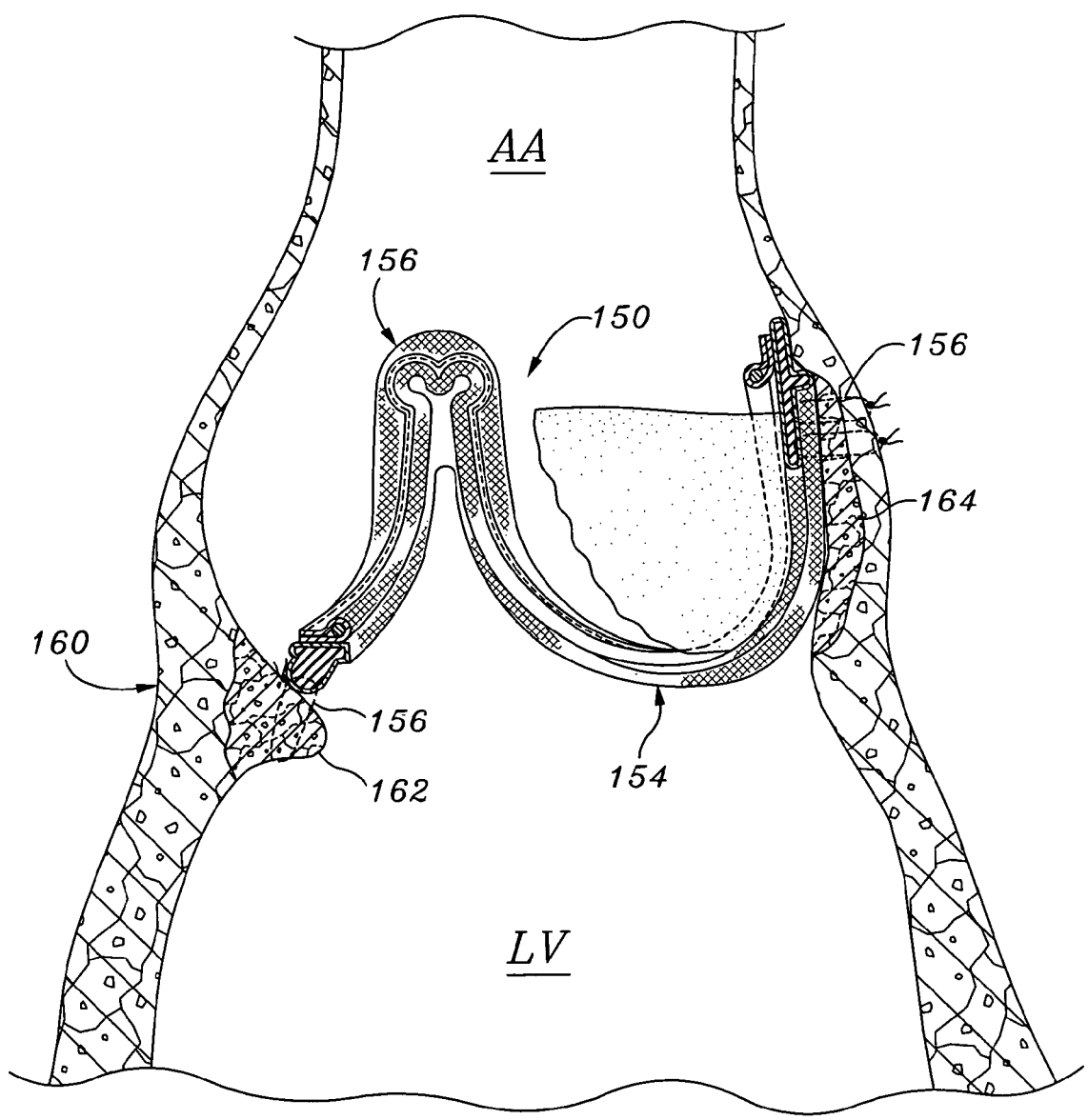
FIG. 10 is a sectional view of the exemplary prosthetic heart valve of FIG. 7 shown implanted in an aortic annulus.
Figure 11:
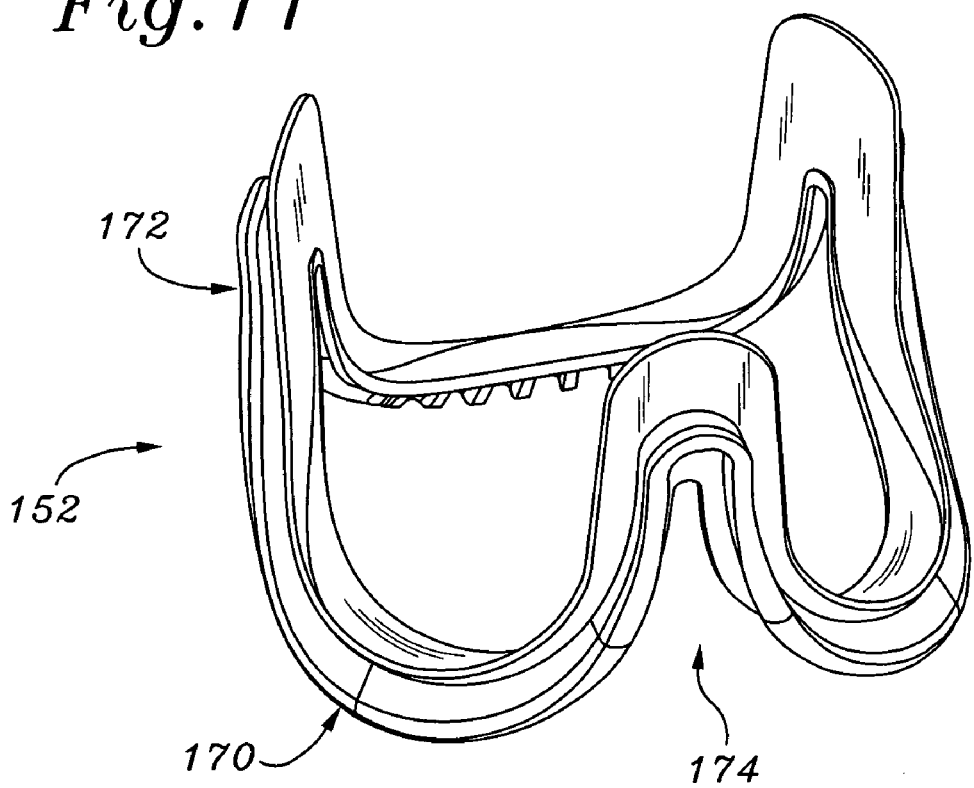
FIG. 11 is a perspective view of an alternative connecting band for use with a flexible heart valve of the present invention.
Figure 12:
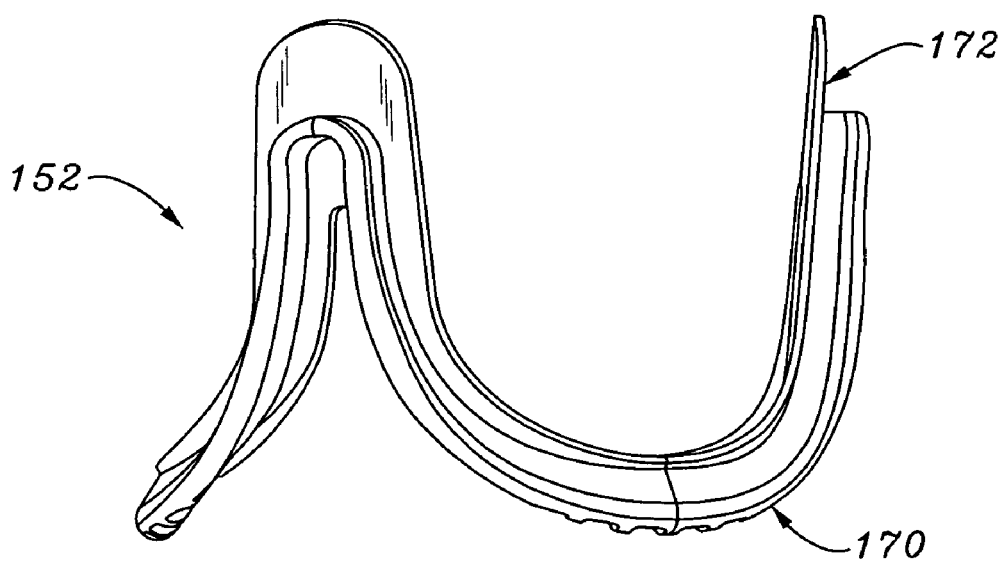
FIG. 12 is a left side elevational view of the connecting band of FIG. 11.
Figure 13:
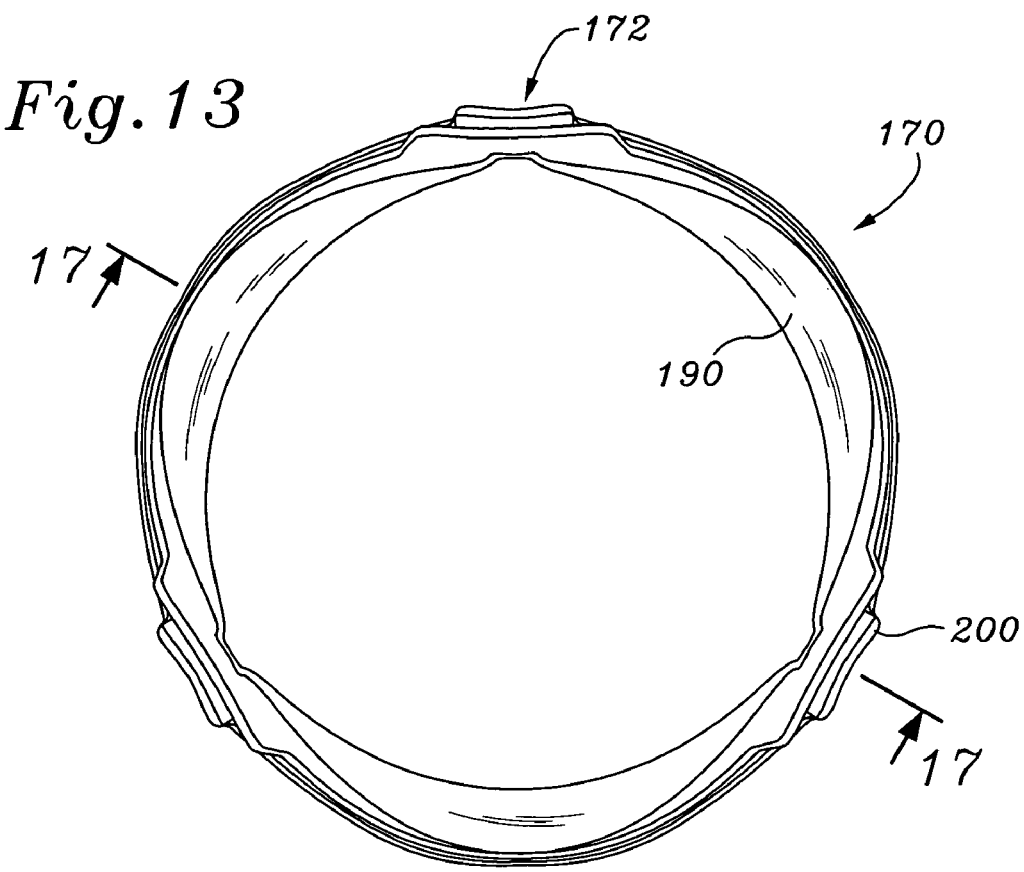
FIG. 13 is a top plan view of the connecting band of FIG. 11.
Figure 14:
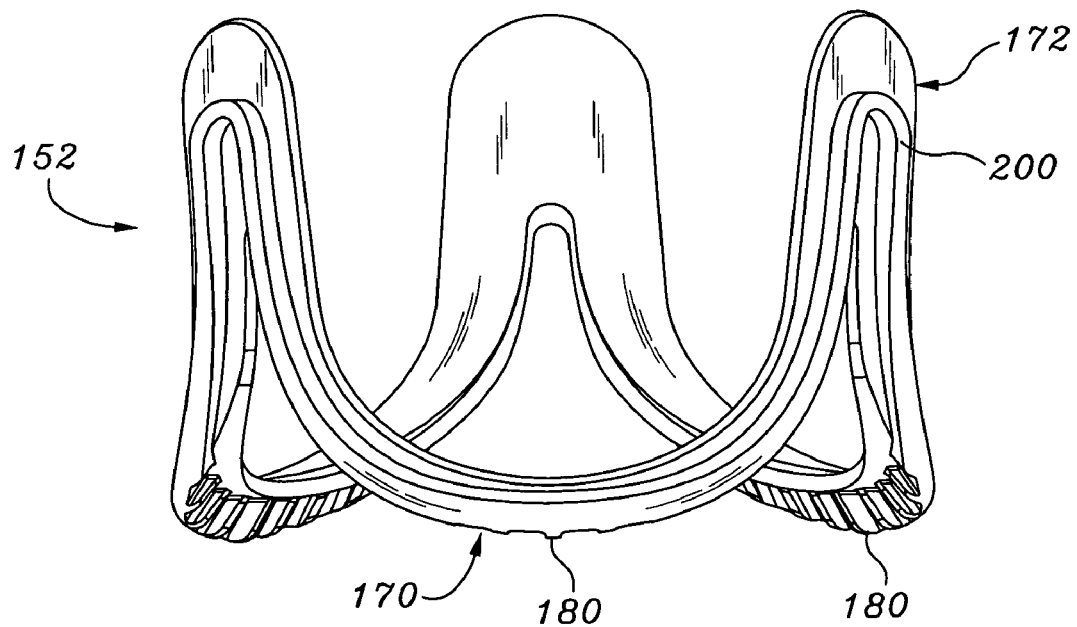
FIG. 14 is a rear elevational view of the connecting band of FIG. 11.

The present invention provides an alternative prosthetic valve 150 seen implanted in a supra-annular position in FIG. 10 that incorporates a connecting band 152 seen in FIGS. 11-17. The prosthetic valve 150 is constructed in the same manner as the prosthetic valve 40 of FIGS. 3-9, with the substitution of the alternative connecting band 152 for the earlier-described band 42. The region of the heart depicted shows the left ventricle LV at the bottom separated from the ascending aorta AA at the top by the aortic annulus 160. As described above, the aortic annulus 160 is primarily defined by fibrous tissue that forms an inwardly projecting ledge 162 at the cusps and upwardly projecting commissures 164. The shape of the annulus 160 is undulating with three cusps 162 curved in the inflow direction alternating with three commissures 164 projecting in the outflow direction. The fibrous tissue is cross-hatched differently than the adjacent tissue, although anatomists will understand that there is not always such a clear dividing line between the fibrous and non-fibrous tissues.

The prosthetic heart valve 150 includes alternating cusps 154 and commissures 156 that conform to the native aortic annulus 160. A number of suture stitches 156 are shown attaching the valve 150 to the annulus 160. In a preferred embodiment, standard suture techniques may be used to implant the valve 150 in the supra-annular position as shown. That is, the entire valve 150 attaches to the fibrous tissue defined by the aortic annulus 160, as opposed to continuing up the wall of the ascending aorta AA. Because of the supra-annular positioning, the valve 150 can be sized larger than conventional valves that fit within the annulus, or in an intra-annular position. Consequently, the size of the orifice defined by the annulus 160 is not unduly constricted. Furthermore, the flexibility of the valve 150 and attachment up the commissures 164 enables it to match the reciprocating motions of the different parts of the annulus 160, as was described with respect to FIGS. 1 and 2.

Figure 19:
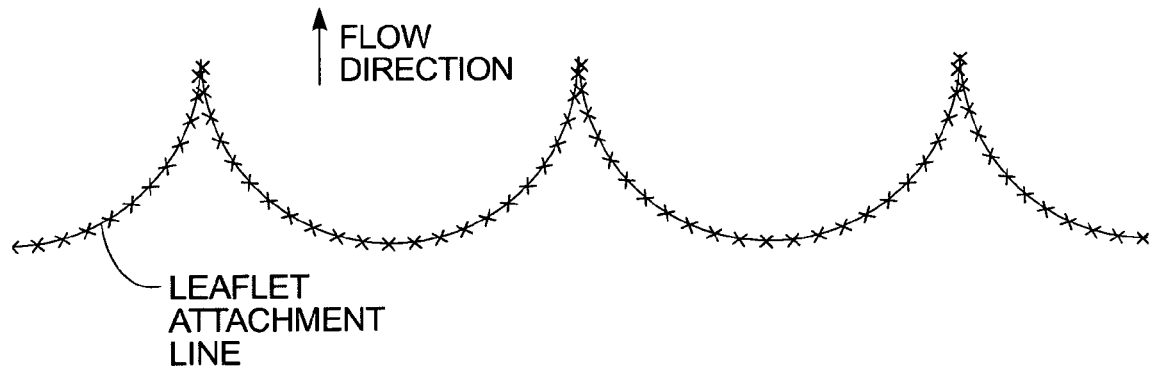
FIG. 19 schematically illustrates a preferred supra-annular suture placement relative to a solid leaflet attachment line.

FIG. 19 schematically illustrates a preferred supra-annular suture placement relative to a solid leaflet attachment line. The Xs indicate placement of sutures or staples to attach the prosthetic valve 150. Because the line of sutures corresponds to the line of native leaflet attachment, none of the sutures extends into the tissue of the ascending aorta. Furthermore, as will be explained below, the alternative connecting band 152 provides features that permit supra-annular suture placement and which will maintain the position of the prosthetic valve 150 without allowing it to slide into an intra-annular position. Finally, the connecting band 152 remains highly flexible such that the resulting valve 150 accommodates relative movement of the adjacent annulus and sinuses.

Figure 15:
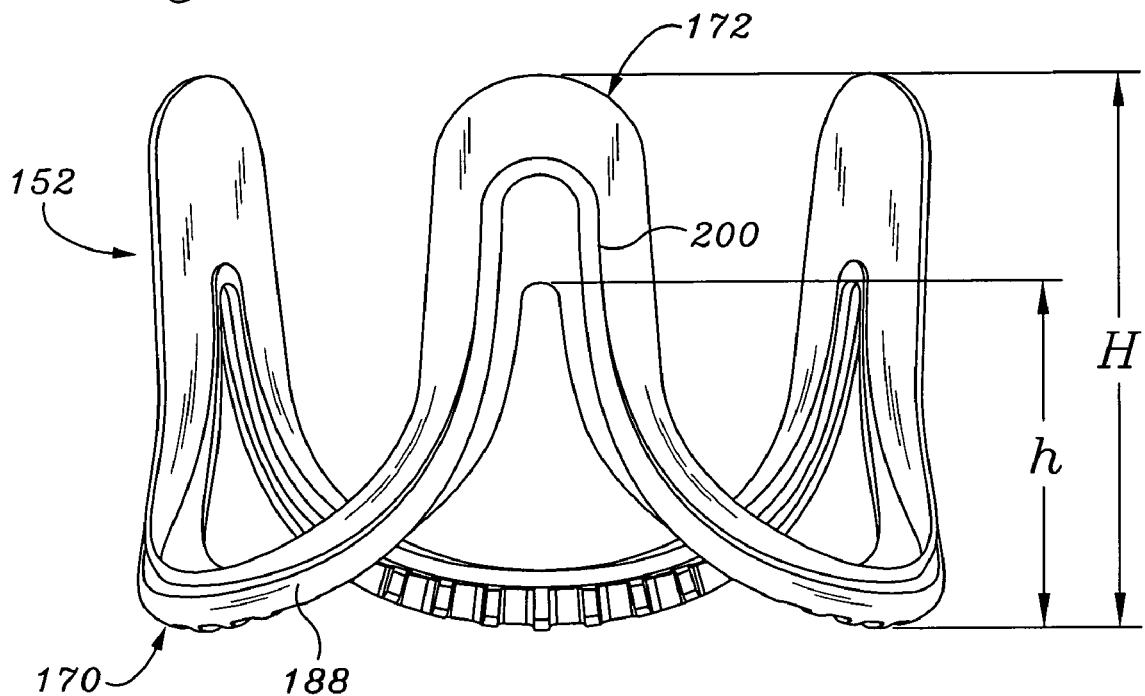
FIG. 15 is a front elevational view of the connecting band of FIG. 11.

With reference now to FIGS. 11-17, the alternative connecting band 152 includes the familiar alternating cusp 170 and commissure 172 shape. Indeed, the overall undulating shape of the connecting band 152 is much like the connecting band 42 seen in FIG. 3. In this regard, generally axially-oriented gaps 174 are again defined between the cusps 172 enabling flexing of the valve 150 once implanted. As seen in FIG. 15, the height h of each of the gaps 174 is preferably at least about 50%, preferably between about 55%-75%, of the entire axial height H of the connecting band 152, and a ratio of about 65%, is most desirable. Furthermore, gap ratios (h/H) may differ depending on the size of valve. Specific examples are: 59% for 19 mm valves, 64% for 23 mm valves, and 69% for 29 mm valves.

Figure 16:
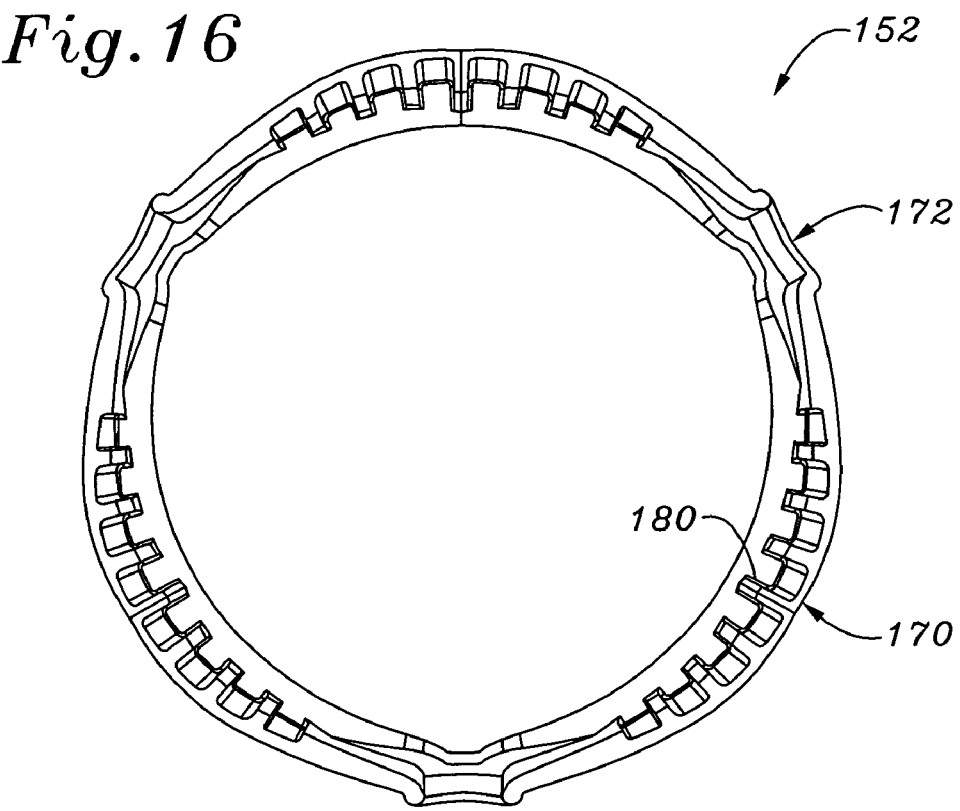
FIG. 16 is a bottom plan view of the connecting band of FIG. 11.
Figure 17:
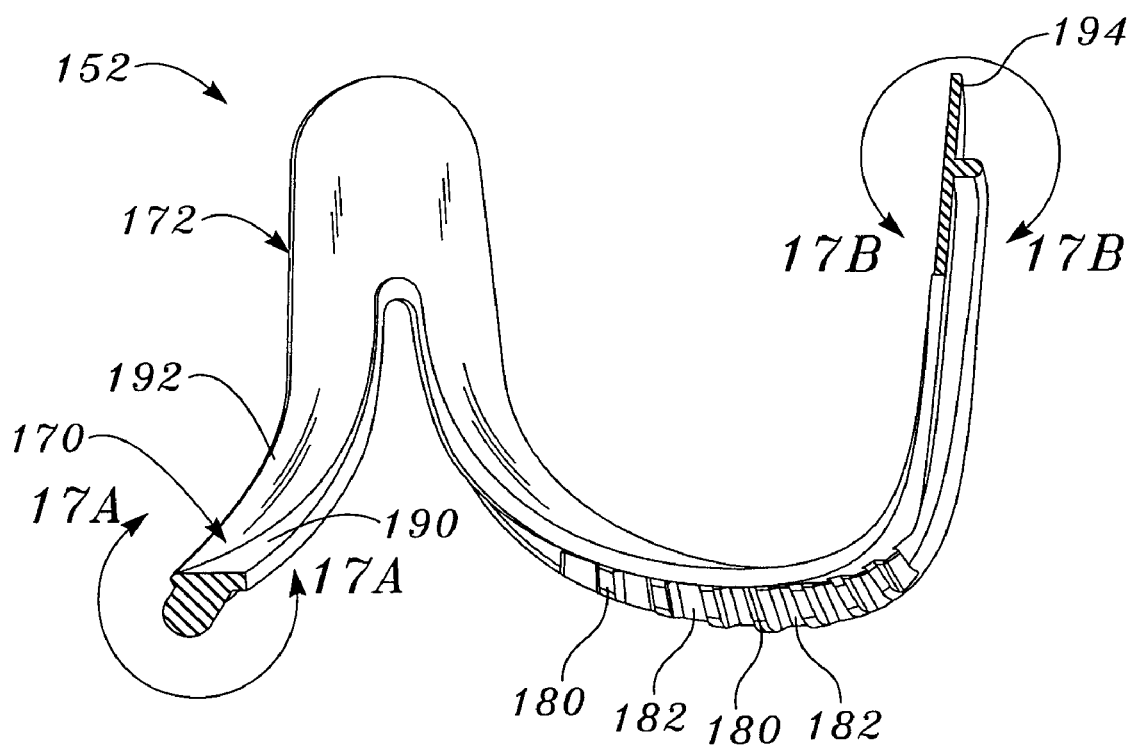
FIG. 17 is a sectional view of the connecting band of FIG. 11 taken along line 17-17 of FIG. 13 and illustrating preferred cross-sectional shapes at both the cusps and commissures.

Looking at FIG. 17 and the enlargements of 17A and 17B, a preferred configuration of the connecting band 152 is shown which includes radially thick cusps 170 separated by radially thin commissures 172. The cross-section 17A is taken through the apex of one of the cusps 170 and also through one of a plurality of radial ribs 180 separated by grooves 182 provided on the inflow side thereof. The bottom plan view of the connecting band 152 of FIG. 16 illustrates the circumferential spacing of these radial ribs 180, while various views show their relative size and contours. The apex of the cusp 170 includes a flat upper or outflow surface 184 that extends inward to a lip 186. The shape of the radial ribs 180 includes a radially outwardly angled projection or lobe 188 that defines the inflow end of the connecting band 152. As seen best in FIG. 16, the size of the radial ribs 180 gradually diminishes from the apex toward each adjacent commissures 172. FIG. 17 illustrates the distance to which the ribs 180 extend toward the commissures 172. Essentially, the ribs 180 are provided in the portion of the cusps 170 that extends along a gradual curve at the inflow end, and they terminate at a point at which the connecting band 152 exhibits a marked curvature toward the axial direction, continuing to the commissures 172.

Figure 17A:
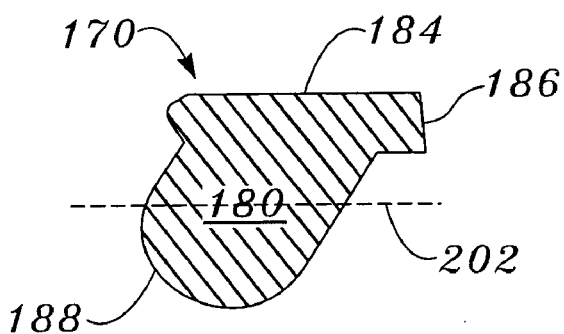
FIGS. 17A and 17B are enlarged cross-section sectional views of the connecting band of FIG. 17.
Figure 17B:
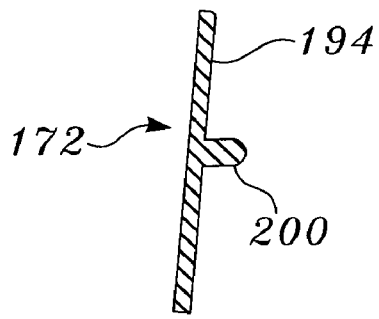

FIG. 17 also illustrates the transition between the apex of the cusps 170 and the commissures 172. The connecting band 152 is primarily oriented in a radial direction at the cusp apex, but it has a substantially axial component in the commissures 172. The outflow surface 184 and the cusp apex is defined by a radially inward shoulder or ledge 190 that gradually disappears toward each commissure 172. In contrast, an outwardly directed flap or free margin 192, which is not present at the cusp apex, commences on both sides of the cusp apex and increases in size toward each commissure 172. In the cusps 170, the free margin 192 projects radially outward and in the outflow direction, much like the free margin 96 seen in FIG. 5A. The free margin 192 then transitions from the outwardly angled orientation to a substantially axially-oriented free margin 194 at the commissures 172. FIG. 17B depicts the shape and slightly outwardly angled orientation of the free margin 194 at the commissures. Though the illustrated free margin 192, 194 gradually diminishes in size from each commissure 172 to an apex of each cusp 170, the free margin may also remain a constant radial width around the periphery of the connecting band 152.

The ledge 190 functions to receive a stent/leaflet sub-assembly, such as that shown at 110 in FIG. 6. When the entire valve is assembled, the ledge 190 prevents the stent/leaflet sub-assembly from migrating downward with respect to the connecting band 152. That is, the greatest axial forces experienced by the implanted valve, at least in the aortic position, are generated during diastole when the left ventricle fills and the aortic leaflets close. High pressure within the ascending aorta and reduced pressure in the left ventricle imparts an axial force in the inflow direction to the prosthetic valve. Because the stent/leaflet sub-assembly is securely attached to the connecting band 152 with the ledges 190 conforming to and on the inflow side of each of the cusps of the sub-assembly, the entire valve assembly maintains its integrity over time.

With reference now to FIG. 15, the connecting band 152 also features an outwardly-directed reinforcing flange 200 in the middle of and tracing the shape of the commissures 172. That is, the reinforcing flange 200 has an inverted U-shape. The free margin 194 at the commissures 172 projects axially and circumferentially beyond the reinforcing flange 200 as shown. In the preferred embodiment, the outwardly-directed lobe 188 at the cusps 170 and the reinforcing flange 200 form a continuous undulating reinforcing ridge or bulge around the periphery of the connecting band 152. The size of this continuous ridge is largest at the cusp apex, as seen in FIG. 17A, and smallest at the top of the commissures 172, as seen in FIG. 17B. This continuous ridge provides sufficient mass within the connecting band 152 to permit the supra-annular placement with annular suture techniques. That is, in contrast with earlier connecting bands, such as the band 42 of FIGS. 3-9, the connecting band 152 provides a sewing ridge on its inflow side that the surgeon can feel and grasp and pass sutures through using the annular suture technique. The ridge is most prominent at the midpoint of the cusps 170 corresponding to the native annulus cusps, but also extends up the commissures 172 as the reinforcing flange 200 which can be sewn to the upstanding fibrous commissures, as seen in FIG. 10.

Despite the provision of this continuous sewing ridge, the connecting band 152 remains highly flexible and avoids unduly limiting the correspondent motion of a flexible heart valve made therewith. In the first embodiment, radial slots were provided around the cusps to enhance their flexibility. In the embodiment of FIGS. 11-17 the sewing ridge is discontinuous at the cusps and continuous at the commissures. The connecting band 152 provides the grooves 182 in between each of the radial ribs 180 on the inflow side of the cusps 170. These grooves provide relief points that improve the compliance of the connecting band 152 without sacrificing the beneficial sewing ridge provided by the intermittent ribs 180. Much like the first-described embodiment, each cusp 170 has a varying cross-section between adjacent commissures 172 that includes at least one relief point (slits 102 or grooves 182) at which the cross-section abruptly reduces such that bending of the connecting band cusps occurs first at the relief point. Furthermore, the aforementioned free margin 192 decreases to nothing at the apex of each cusp 170, as seen in FIG. 17A. As the forces on the connecting band 152 primarily act to spread apart the commissures 172, this reduction in the free margin 192 greatly enhances the necessary flexibility of the cusps 170. Much like the earlier-described embodiment, each cusp 170 has a radial cross-section that gradually diminishes in area moment of inertia relative to a bending plane 202 (FIG. 17A) that extends perpendicular to the flow axis of the connecting band 152.

Though the illustrated sewing ridge (comprising the outwardly-directed lobe 188 and reinforcing flange 200) gradually increases in size from the end of each commissure 172 to an apex of each cusp 170, the sewing ridge may also exhibit a constant radial width around the periphery of the connecting band 152. The important point is that the sewing ridge is large enough for ease-of-use for surgeons to pass a suture through, and as small as possible to minimize bulk in the flow tract.

Also it should be large enough and compliant enough to fit in the native anatomy without leaking. The cusp area is larger to allow it to be more adaptable at the base where removal of calcified leaflets and surrounding calcification often leaves a ragged edge.

The present invention may be embodied in other specific forms without departing from its spirit or essential characteristics. The described embodiments are to be considered in all respects only as illustrative and not restrictive. In particular, though the flexible nature of the present heart valve has been described as being particularly suitable for use in the aortic position, the advantage of flexibility could equally apply to a valve implanted in other positions, such as the mitral position. The scope of the invention is, therefore, indicated by the appended claims rather than by the foregoing description. All changes which come within the meaning and range of equivalency of the claims are to be embraced within their scope.

What is claimed is:

1. A suture-permeable connecting band for securing a prosthetic heart valve to an anatomical cavity, comprising:
    a flexible, continuous connecting band having an undulating shape generally defining a tube with alternating inflow cusps and outflow commissures, the cusps having large radii of curvatures relative to the commissures, an inflow edge of the connecting band substantially conforming to an outflow edge thereof and following the undulating shape such that axial gaps are created between adjacent cusps at the commissures, the gaps having a height of at least about 50% of the overall axial height of the connecting band, wherein each cusp has a varying cross-section between adjacent commissures that includes at least one relief point comprising a generally radial slit formed by a gapless cut in the connecting band at which the cross-section abruptly reduces such that bending of each connecting band cusp occurs first at the relief point.

2. The heart valve connecting band of claim 1, wherein there are a plurality of the generally radial slits provided in each connecting band cusp.

3. The heart valve connecting band of claim 2, wherein there are between 5-7 of the generally radial slits provided in each connecting band cusp.

4. The heart valve connecting band of claim 1, wherein the connecting band is molded of silicone rubber.

5. The heart valve connecting band of claim 1, further comprising:
    a continuous sewing ridge provided around the periphery of the connecting band that facilitates supra-annular attachment of the prosthetic valve, the sewing ridge being radially-outwardly directed at the commissures and larger and angled radially outward and toward the inflow end at the cusps.

6. The heart valve connecting band of claim 5 wherein the connecting band defines a free margin comprising a relatively narrow flap that angles radially outward and toward the outflow end at the cusps, and is substantially axially-aligned at the commissures.

7. The heart valve connecting band of claim 6, wherein the free margin gradually diminishes in size from each commissure to an apex of each cusp.

8. The heart valve connecting band of claim 6, wherein the free margin at the commissures projects axially and circumferentially beyond the sewing ridge.

9. The heart valve connecting band of claim 5, wherein the sewing ridge at the cusps defines an inflow end of the connecting band and includes a plurality of alternating generally radial ribs and grooves.

10. The heart valve connecting band of claim 9, wherein the size of the generally radial ribs varies and is greatest at an apex of each cusp.

11. The heart valve connecting band of claim 10, wherein the size of the ribs and grooves diminishes from a maximum at an apex of the cusps until they disappear prior to the commissures.

12. The heart valve connecting band of claim 5, wherein the sewing ridge is discontinuous at the cusps and continuous at the commissures.

13. The heart valve connecting band of claim 1, wherein the cusps of the connecting band each includes an inner ledge and an upwardly angled free margin, and wherein the slit is formed in the free margin and opens to the outflow edge thereof.

14. The heart valve connecting band of claim 13, wherein the slit extends from the outflow edge of the free margin to a corner between the free margin and the inner ledge.

15. The heart valve connecting band of claim 13, wherein the upwardly angled free margins form their greatest outward angle with respect to a central axis of the connecting band at each cusp and gradually re-align to be parallel to the central axis in the commissures.

16. The heart valve connecting band of claim 13, wherein there are a plurality of the generally radial slits provided in each connecting band cusp.

17. The heart valve connecting band of claim 16, wherein there are between 5-7 of the generally radial slits provided in each connecting band cusp.

18. The heart valve connecting band of claim 1, wherein the slit opens to the inside radius of the curvature of each cusp.

* * * * *